United States Patent

Leininger et al.

US006927308B2

(10) Patent No.: US 6,927,308 B2
(45) Date of Patent: Aug. 9, 2005

(54) METHOD FOR SYNTHESIS OF OXIMES

(75) Inventors: Stefan Leininger, Hanau (DE); Juergen Herwig, Huenxe (DE); Martin Roos, Haltern (DE); Georg Oenbrink, Duelmen (DE)

(73) Assignee: Degussa AG, Duesseldorf (DE)

( * ) Notice: Subject to any disclaimer, the term of this patent is extended or adjusted under 35 U.S.C. 154(b) by 46 days.

(21) Appl. No.: 10/733,278

(22) Filed: Dec. 12, 2003

(65) Prior Publication Data

US 2004/0167359 A1 Aug. 26, 2004

(30) Foreign Application Priority Data

Dec. 23, 2002 (DE) .......................................... 102 60 717

(51) Int. Cl.⁷ ...................... C07C 249/08; C07C 249/14
(52) U.S. Cl. .................. 564/259; 564/262; 564/264
(58) Field of Search ................................ 564/259, 262, 564/264

(56) References Cited

U.S. PATENT DOCUMENTS

| | | | |
|---|---|---|---|
| 4,745,221 A | 5/1988 | Roffia et al. | |
| 4,794,198 A | 12/1988 | Roffia et al. | |

FOREIGN PATENT DOCUMENTS

| | | | | |
|---|---|---|---|---|
| DE | 195 21 011 | 12/1995 | | |
| DE | 100 47 435 | 4/2002 | | |
| DE | 101 03 581 | 8/2002 | | |
| DE | 101 42 620 | 3/2003 | | |
| EP | 0 208 311 | 1/1987 | | |
| EP | 0 299 430 | 1/1989 | | |
| EP | 0 496 385 | 7/1992 | | |
| EP | 0 564 040 A2 * | 10/1993 | ......... | C07C/249/04 |
| EP | 0 690 045 | 1/1996 | | |
| EP | 0 735 017 | 10/1996 | | |
| EP | 1 138 387 | 10/2001 | | |
| GB | 1 113 619 | 5/1968 | | |

\* cited by examiner

*Primary Examiner*—Brian Davis
(74) *Attorney, Agent, or Firm*—Oblon, Spivak, McClelland, Maier & Neustadt, P.C.

(57) ABSTRACT

An oxime is synthesized by ammoximation of a carbonyl compound. In stage (i) of the process, a carbonyl compound containing 6 to 20 C atoms is reacted with ammonia and hydrogen peroxide in the presence of a) an organic solvent that is a1) at least partly water-soluble, a2) stable under ammoximation conditions, a3) has a boiling point of higher than 100° C. and/or is capable of forming a two-phase azeotrope with water, and b) a titanium-containing heterogeneous catalyst. After the reaction, the catalyst is separated from the reaction mixture. The oxime is crystallized and separated from the reaction mixture. Water is removed from the remaining mother liquor, provided the mother liquor is a two-phase system in which one of the phases is an aqueous phase. Water or a water-containing two-phase azeotrope is distilled off from the mother liquor, while the distillation bottoms and, optionally, the predominantly organic phase of the azeotrope are recycled to stage (i).

20 Claims, 2 Drawing Sheets

METHOD FOR SYNTHESIS OF OXIMES

BACKGROUND OF THE INVENTION

1. Field of the Invention

The present invention relates to a method for synthesis of an oxime by ammoximation of a carbonyl compound containing 6 to 20 C atoms.

2. Discussion of the Background

European Patent Applications 0208311, 0496385, 0299430 and 0564040 as well as U.S. Pat. No. 4,745,221 teach the ammoximation of carbonyl compounds, especially alkanones and cycloalkanones, using hydrogen peroxide and ammonia in the presence of a heterogeneous catalyst composed of the elements silicon, titanium and oxygen. Complete conversions and corresponding simple workup and recovery of the organic solvent used are described only for the ammoximation of cyclohexanone. As is known, cyclohexanone oxime is the raw material for caprolactam synthesized by the Beckmann rearrangement.

During the ammoximation of sterically bulky ketones such as alkanones or cycloalkanones containing more than 6 carbon atoms, the yields are generally relatively low, reflecting the relatively low reaction rates and relatively low hydrogen peroxide selectivities. To overcome these disadvantages it has been proposed that the catalyst system be supplemented by further components, to be referred to as cocatalysts hereinafter. For example, amorphous silicates have been described as cocatalysts in German Patent 19521011, as have acid solids in unexamined German patent application 10047435 and ammonium ions in unexamined German patent application 10103581.

As described in unexamined German patent applications 10047435 and 10103581, the ammoximation of large and sterically shielded alkanones and cycloalkanones becomes sufficiently fast and selective if the reaction is performed in the presence of a suspension catalyst and of an organic solvent that is completely or partly miscible with water, especially a short-chain alcohol containing 1 to 6 carbon atoms.

In the described ammoximation, the alkanone or cycloalkanone used reacts with ammonia and hydrogen peroxide on titanium silicalite to form the corresponding oxime.

In addition to the ammoximation, secondary oxidation reactions between hydroxylamine formed in a parallel reaction and hydrogen peroxide—see U.S. Pat. No. 4,745,221—can lead to formation of byproducts that lower the peroxide selectivity, such as dihydroxylamine, nitrosyl, nitrous acid, nitric acid and nitrous oxide. It has also been observed that peroxide selectivity relative to the formed oxime decreases with increasing conversions of alkanones and cycloalkanones, and that complete conversions can be achieved only with simultaneously greater formation of byproducts.

Consequently, the content of water in the reaction mixture increases during the reaction. Since the solubility of long-chain and/or sterically bulky alkanones and cycloalkanones such as cyclooctanone and cyclododecanone as well as of their corresponding oximes decreases sharply with increasing water content in the reaction mixture, it is advisable to limit the quantity of water as much as possible during ammoximation. This is achieved by using hydrogen peroxide of the highest possible concentration in aqueous solution together with ammonia as dry gas.

In order to improve the conversion, it is of interest to minimize side reactions that produce water and lower peroxide selectivity, by choosing catalysts for application alone or if necessary in combination with cocatalysts.

As can be inferred from numerous documents, ammoximation is followed by distillative and/or extractive workup of the reaction mixture—see, for example, European Patents 0496385, 0208311, 0690045 and 0735017 as well as U.S. Pat. No. 4,794,198.

In a process having closed or partly closed solvent recycle, or in other words during continuous ammoximation, the water introduced and formed during the reaction must be additionally separated in an integrated or separate workup step, in order that the organic solvents present can be recycled to the ammoximation stage.

A disadvantage of distillative workup is that practically the entire solvent mixture must be distilled, thus consuming considerable energy and reducing the economy of the process.

Another disadvantage of reaction solutions containing higher molecular weight oximes is that separation of the carbonyl compound and its oxime from one another by distillation is incomplete or nonexistent. In such cases, therefore, it is of great interest to achieve the most complete ketone conversion possible, in order to be able to obtain oximes with the lowest possible carbonyl content.

In German Patent Application 10142620, there is described a method superior to distillative workup for separation of the oxime from the reaction mixture. The oxime is separated from the reaction mixture by crystallization, and the mother liquor is freed at least partly of water by subsequent pervaporation or vapor permeation by using at least one membrane separating stage. A disadvantage here is that, in the case of oximation of ketones with relatively high molecular weights under conditions of incomplete ketone conversion, the membranes can rapidly become fouled by ketone deposits and/or by deposits of ammonium salts present as cocatalysts, whereby expensive cleaning or even replacement of the membranes is necessary.

SUMMARY OF THE INVENTION

It is an object of the present invention to provide a method for the synthesis of oximes. In particular it is an object of the present invention to provide a method that comprises ammoximation of a carbonyl compound with ammonia and hydrogen peroxide in the presence of a titanium-containing catalyst, isolation of the oxime from the reaction mixture by crystallization, discharging water from the system and recycling of the organic solvent to the ammoximation, and that does not suffer from the disadvantages of a membrane-separation stage.

Another object is that the method should be particularly suitable for synthesis of oximes containing more than 6 C atoms, especially cyclic oximes containing 8 to 12 C atoms.

Yet another object is that the ammoximation itself will be possible in known manner and will not be detrimentally influenced by the steps for workup.

It has been surprisingly found that the said objects can be achieved by using specially selected solvents.

This and other objects have been achieved by the present invention the first embodiment of which includes a method for synthesis of an oxime by ammoximation of a carbonyl compound, comprising:

(i) reacting a carbonyl compound containing 6 to 20 C atoms with ammonia and hydrogen peroxide in the presence of a) an organic solvent that is a1) at least partly water-soluble, a2) stable under ammoximation conditions, a3)

has a boiling point of higher than 100° C. and/or is capable of forming a two-phase azeotrope with water, and b) a titanium-containing heterogeneous catalyst, to obtain a reaction mixture containing said oxime, (ii) separating the catalyst from the reaction mixture, (iii) crystallizing the oxime and separating the crystallized oxime from the reaction mixture, thereby obtaining crystallized oxime and a mother liquor, (iv) if the mother liquor is a two-phase system in which one of the phases is an aqueous phase, then water is removed from the mother liquor in the form of an aqueous phase, and (v) distilling off water or a water-containing two-phase azeotrope from the mother liquor, while the distillation bottoms and, optionally, the predominantly organic phase of the azeotrope are recycled to stage (i).

DETAILED DESCRIPTION OF THE INVENTION

The subject matter of the present invention is therefore a method for synthesis of oximes by ammoximation of carbonyl compounds, comprising (i) reaction of a carbonyl compound containing 6 to 20 C atoms with ammonia and hydrogen peroxide in the presence of an organic solvent that is at least partly water-soluble and of a titanium-containing heterogeneous catalyst, (ii) separation of the catalyst from the reaction mixture, (iii) crystallization of the oxime and separation of same from the mother liquor, (iv) transfer of water out of the mother liquor and (v) recycling of the solvent to stage (i), wherein in stage (i) a solvent is used that is stable under ammoximation conditions, has a boiling point of higher than 100° C. and/or forms a two-phase azeotrope with water, and wherein water or a water-containing two-phase azeotrope is distilled off from the mother liquor, while the distillation bottoms and, if desired, the predominantly organic phase of the azeotrope are recycled to stage (i).

According to a first embodiment, solvents whose boiling point is higher than 100° C., especially higher than 110° C., and particularly preferably ranges from 110 to 200° C. are used. The boiling point includes all values and subvalues therebetween, especially including 105, 110, 115, 120, 125, 130, 135, 140, 145, 150, 155, 160, 165, 170, 175, 180, 185, 190 and 195° C. Under the ammoximation conditions, monohydric or polyhydric alcohols having the necessary water solubility and stability are suitable in particular. Preferred examples are n-amyl alcohols, isoamyl alcohols and hexanols, provided they do not form an azeotrope with water. Particularly suitable, however, are ethylene glycol, 1,2-propylene glycol, 1,3-propylene glycol, 1,2-butanediol, 1,4-butanediol, 1,5-pentanediol and 1,6-hexanediol. Such diols are easy to handle, and in principle triols such as glycerin can also be used. Diols having primary hydroxyl groups are preferred, especially ethylene glycol and 1,3-propylene glycol.

According to a second embodiment, the solvents, and especially alcohols in this case, form with water azeotropes that boil below 100° C. and that condense as two phases, one phase being rich (>50%) in water. Particularly suitable examples are butanols and amyl alcohols, especially n-butanol, tert-butanol and isoamyl alcohol. n-Butanol is especially suitable, because the two-phase azeotrope permits easy separation of water from the mother liquor.

The crystallization of the oxime from the ammoximation reaction mixture can be performed in the same way as described in unexamined German patent application 10142620.8, and so the full contents thereof are incorporated by reference into the disclosure of this invention.

The overall method will be further explained with reference to FIG. 1, which illustrates a process diagram.

Figure 2:
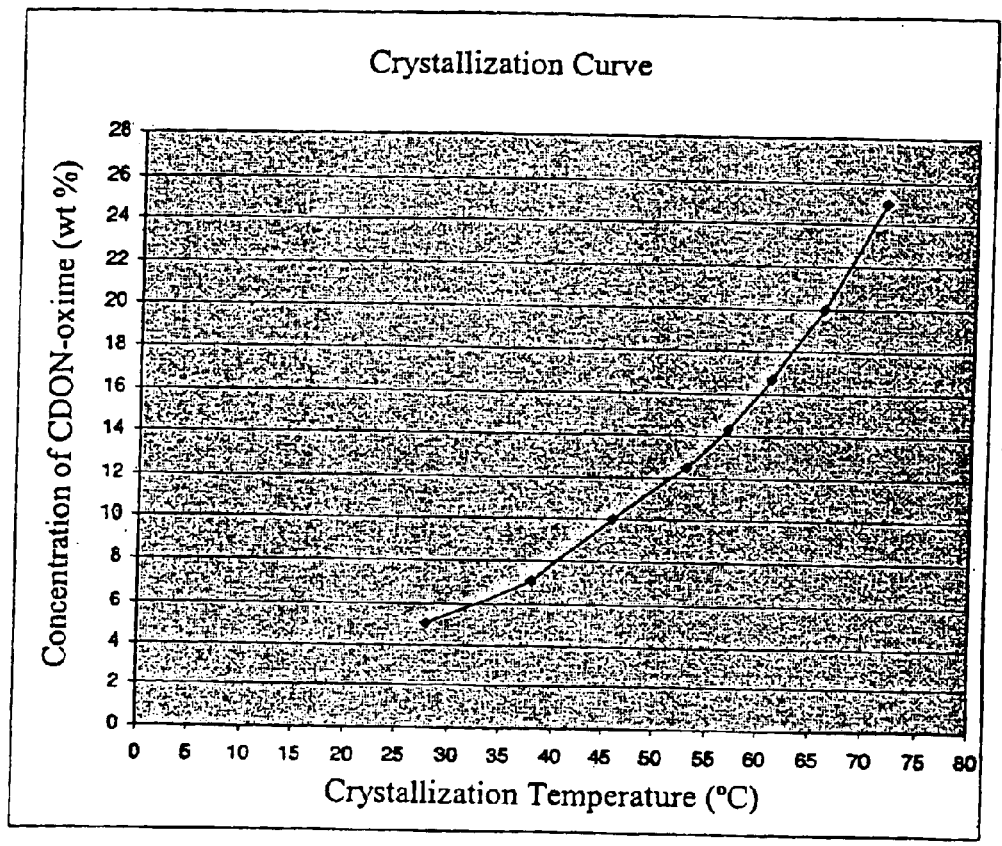
FIG. 2 shows, as a function of temperature, a crystallization curve of cyclododecanone oxime (CDON oxime).

FIG. 2 shows, as a function of temperature, for n-butanol mixed with 10 wt % of water as the solvent, a crystallization curve of cyclododecanone oxime (CDON oxime). The method of the present invention is particularly suitable for the synthesis of cyclododecanone oxime (CDON oxime).

Figure 1:
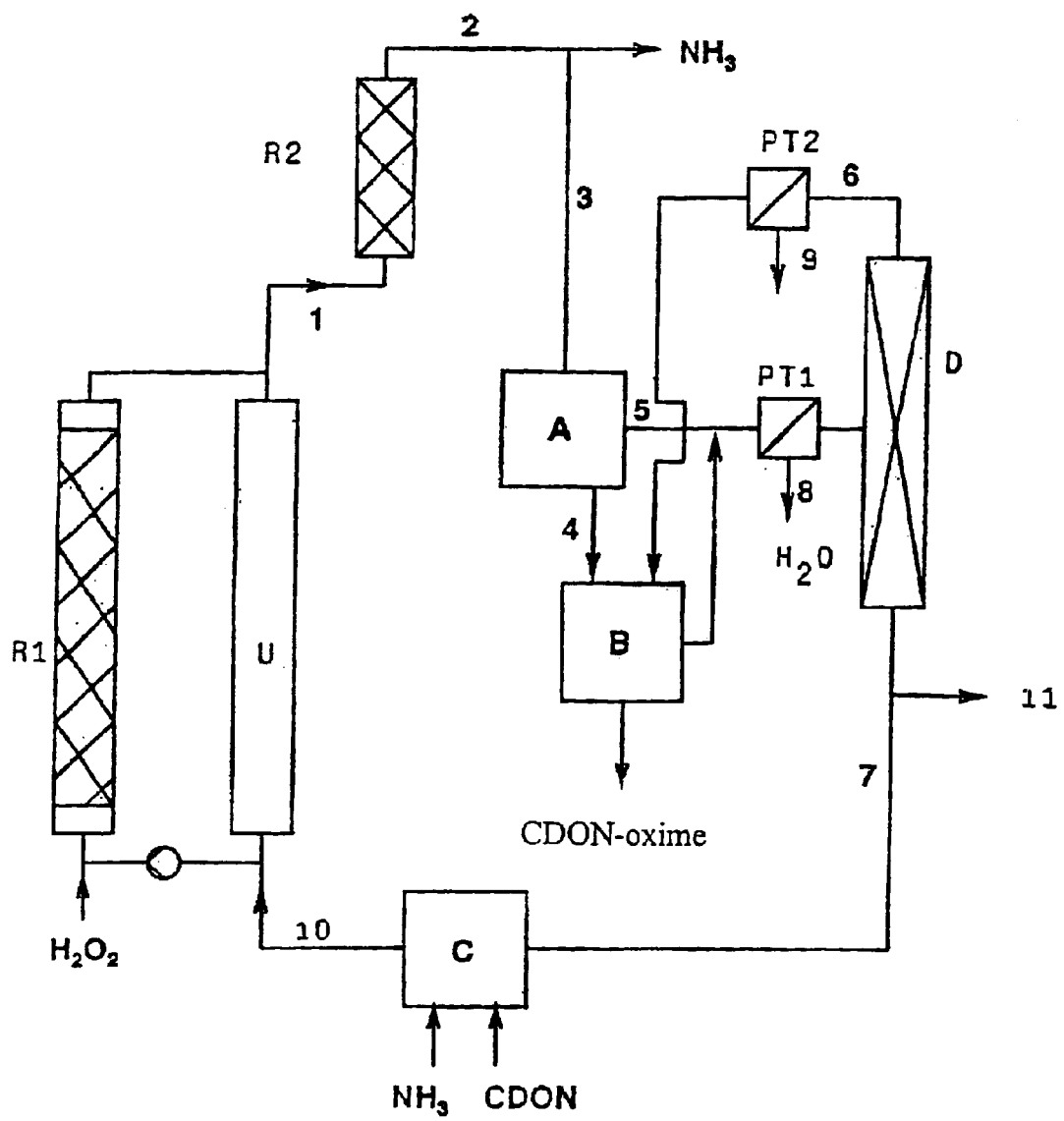
FIG. 1 illustrates a process diagram.

In FIG. 1, a preferred embodiment of the apparatus, the symbols have the following meanings: R1 denotes an ammoximation reactor, which may have one or more stages. It may be a fixed-bed or suspension reactor—a fixed-bed reactor being illustrated. R2 is a secondary reactor to complete the reaction and U is a circulation line, in which the reaction mixture can also be cooled or heated. A stands for a crystallization and separation apparatus for separation of the crystals (=oxime) from the mother liquor. B stands for a washing apparatus with downstream solid/liquid separation. D stands for a distillation apparatus for direct or azeotropic removal of water by distillation. PT1 and PT2 denote separation units for separation of two liquid phases.

The ammoximation can be performed continuously or batchwise with complete or incomplete ketone conversion. Besides flow and circulation reactors containing a catalyst fixed bed, the reaction can also be performed in the presence of a suspension catalyst. A solid/liquid separation unit must be connected downstream from the reaction in the last case and is optional in the first case, for the purpose of being able to separate suspension catalyst or fines from the ammoximation mixture and to feed the resulting solid-free reactor discharge (1) or (2) to workup.

The reactor discharges (1) and (2) contain not only the formed oxime in the selected aqueous organic solvent system but also unreacted starting materials, or in other words the carbonyl compound, hydrogen peroxide and ammonia, as well as byproducts.

If so desired, the ammonia present in reactor discharge (2) can be partially removed from solution in the form of gaseous ammonia, by depressurization to normal pressure, and then collected in a separate stage by condensation and recycled to the apparatus after purification, if such is desired.

Reactor discharge (3), depleted of ammonia, is cooled in a crystallization apparatus (A), wherein the corresponding oxime is crystallized out in the purity needed for the subsequent Beckmann rearrangement. The crystallization apparatus can be designed in any manner familiar to the person skilled in the art, both batchwise and continuous units being usable. The crystallizer is usually operated at temperatures of between −40° C. and +60° C., advantageously of between −10° C. and +30° C. Cold water or refrigerated brine are preferred as cooling fluid. The temperature of the crystallizer includes all values and subvalues therebetween, especially including −35, −30, −25, −20, −15, −10, −5, 0, 5, 10, 15, 20, 25, 30, 35, 40, 45, 50 and 55° C.

The optimal temperature depends on the solubility of the oxime and of the unreacted ketones in the reaction mixture. As an example, FIG. 2 shows the solubility of cyclododecanone oxime as a function of temperature in n-butanol with a water content of 10 wt %.

The crystals (4) separated in a separating apparatus (integrated in (A) in FIG. 1) can be freed of adhering mother liquor by subsequent washing on the separating apparatus or in a separate scrubber (B), using alcohol or an alcohol/water mixture. The oxime is then dried if so desired.

It is a special advantage of the method that, even if a ketone such as cyclododecanone does not react completely, the oxime is obtained in a purity exceeding 99.8% and unreacted ketone can be completely recycled. The oxime obtained in this way can be further processed to the corresponding lactam directly or in a suitable solvent, for example by the Beckmann rearrangement.

In the method according to the present invention, the mother liquor (5) obtained from crystallization followed by phase separation and combined if so desired with the washing solution from subsequent washing generally contains between 0.01 wt % and 5 wt % of oxime, preferably 0.1 wt % to 2 wt % of oxime, 0.01 wt % to 10 wt % of unreacted ketone, preferably 0.1 wt % to 2 wt % of unreacted ketone, 0 wt % to 10 wt % of ammonia and 6 wt % to 20 wt % of water. The amount of oxime in the mother liquor (5) includes all values and subvalues therebetween, especially including 0.05, 0.1, 0.5, 1, 1.5, 2, 2.5, 3, 3.5, 4 and 4.5 wt %. The amount of unreacted ketone in the mother liquor (5) includes all values and subvalues therebetween, especially including 0.05, 0.1, 0.5, 1, 1.5, 2, 2.5, 3, 3.5, 4, 4.5, 5, 5.5, 6, 6.5, 7, 7.5, 8, 8.5, 9 and 9.5 wt %. The amount of ammonia in the mother liquor (5) includes all values and subvalues therebetween, especially including 0.5, 1, 1.5, 2, 2.5, 3, 3.5, 4, 4.5, 5, 5.5, 6, 6.5, 7, 7.5, 8, 8.5, 9 and 9.5 wt %. The amount of water in the mother liquor (5) includes all values and subvalues therebetween, especially including 7, 8, 9, 10, 11, 12, 13, 14, 15, 16, 17, 18 and 19 wt %. Furthermore, the mother liquor may also contain, in concentrations of typically 0.001 mol/l to 0.5 mol/l, preferably 0.01 mol/l to 0.05 mol/l, homogeneously dissolved ammonium salts formed during ammoximation by further oxidation of hydroxylamine and/or used according to unexamined German patent application 10103581 as cocatalysts for the ammoximation. The amount of homogeneously dissolved ammonium salt in the mother liquor includes all values and subvalues therebetween, especially including 0.005, 0.01, 0.05, 0.1, 0.15, 0.2, 0.25, 0.3, 0.35, 0.4 and 0.45 mol/l.

Preferably, if the mother liquor is a two-phase system in which one of the phases is an aqueous phase, then water is preferably removed from the mother liquor in the form of an aqueous phase. In other words, if the mother liquor is already a two-phase mixture, the aqueous phase (8) is separated in a liquid-liquid separating apparatus (PT1) prior to the next process step.

To reduce its water content, the mother liquor (5) or the second phase from an intermediate separating apparatus (PT1) is fed to a distillation apparatus equipped with one or more columns (distillation column (D)) and distilled at temperatures of between 40° C. and 180° C., advantageously of between 80° C. and 140° C. at normal pressure, reduced pressure or slight overpressure, while substantially water or a two-phase azeotrope of water and the solvent as well as ammonia if so desired is separated overhead, depending on the solvent used. The distillation temperature includes all values and subvalues therebetween, especially including 50, 60, 70, 80, 90, 100, 110, 120, 130, 140, 150, 160 and 170° C.

The water content of about 6 wt % to 20 wt % in the mother liquor is usually reduced to 0.01 wt % to 5 wt %, preferably to 0.5 wt % to 2 wt %, and in this form is drawn off as bottom product (7). The reduced water content of the mother liquor includes all values and subvalues therebetween, especially including 0.05, 0.1, 0.5, 1, 1.5, 2, 2.5, 3, 3.5, 4 and 4.5 wt %.

In the case in which a solvent forming an azeotrope with water is used, the two-phase azeotrope (6) distilled off overhead is condensed and then separated in a phase-separating apparatus (PT2). The predominantly organic phase can be recycled directly as solvent to ammoximation and/or can be used as washing solution for subsequent washing of the crystals isolated after crystallization. The predominantly aqueous phase (9), which may still contain small quantities of organic solvent, is dewatered in a further distillation stage or is then discarded as necessary.

The bottom product (7) of distillation, still containing residual oxime, ketone, water and ammonium salts as well as traces of further byproducts and impurities in addition to the solvent, is mixed with fresh ketone in a mixer (C), after which the mixture (10) is recycled to ammoximation. Aqueous hydrogen peroxide is usually fed at one or more points directly into and/or just upstream from the reactor.

In a continuous process using technical-grade starting materials, impurities as well as byproducts of the ammoximation itself can become more concentrated in the course of time. It therefore appears advantageous to separate a partial stream of the distillation bottoms (purge (11)) continuously or batchwise and to remove the impurities and byproducts therefrom by distillation or extraction before recycling it to the ammoximation stage.

The structure of the pellets used as catalyst for a fixed-bed reactor is preferably cylindrical or spherical. Particularly preferred pellets for fixed-bed catalysts are spherical and have a particle diameter ranging from 0.5 to 2.0 mm, especially from 0.8 to 1.6 mm. Preferred cylindrical pellets have a maximum dimension of 2.5 mm and a diameter-to-length ratio ranging from 0.5 to 2. The dimension of the cylindrical pellets includes all values and subvalues between 0.1 and 2.5 mm, especially including 0.2, 0.4, 0.6, 0.8, 1, 1.2, 1.4, 1.6, 1.8, 2, 2.2, and 2.4 mm. The particle diameter of the spherical pellets includes all values and subvalues therebetween, especially including 0.6, 0.7, 0.8, 0.9, 1, 1.1, 1.2, 1.3, 1.4, 1.5, 1.6, 1.7, 1.8 and 1.9 mm. The diameter to length ratio of the cylindrical pellets includes all values and subvalues therebetween, especially including 0.6, 0.7, 0.8, 0.9, 1, 1.1, 1.2, 1.3, 1.4, 1.5, 1.6, 1.7, 1.8 and 1.9 mm.

The titanium-containing catalysts are in particular titanium silicalite in powder, granule, extruded or monolithic form. The catalyst preferably contains titanium silicalite of the general formula $xTiO_2(1-x)SiO_2$, where x is a number that ranges from 0.001 to 0.12, and in particular is larger than 0.01 to 0.1. The value of x includes all values and subvalues therebetween, especially including 0.005, 0.01, 0.05 and 0.1.

The fixed-bed catalysts may contain one or more titanium silicalites and, if necessary, one or more acid solid cocatalysts. Particularly suitable cocatalysts are alumina, titanium dioxide, zirconium dioxide, silicon dioxide and acid zeolites, such as ZSM5. The titanium silicalite or silicalites as well as the cocatalyst or cocatalysts can be used together or in reactors connected in series.

According to a preferred embodiment, the catalysts contain both titanium silicalite(s) and one or more acid cocatalysts, the weight ratio of titanium silicalite to cocatalyst being 99:1 to 1:99 and especially 9:1 to 1:1. The preferred weight ratio of titanium silicalite to cocatalyst includes all values and subvalues therebetween, especially including 8:1, 7:1, 6:1, 5:1, 4:1, 3:1 and 2:1.

The catalyst pellets are produced in a manner known in itself, for example by extrusion of the powder mixture in the presence of water and if necessary an organic and/or inorganic binder, followed by drying and calcining. Examples can be found in European Patent 1138387 A1.

According to a preferred embodiment of the method according to the present invention, the ammoximation takes place in the presence of an ammonium salt that is at least partly soluble in the reaction mixture, the ammonium salt being added or formed in situ from the already present ammonia and an added acid. Non-limiting examples of ammonium salts include: ammonium nitrite, ammonium nitrate, ammonium salts of carboxylic acids, especially ammonium acetate, hydroxyl ammonium nitrite, hydroxyl ammonium nitrate, hydroxyl ammonium acetate, monoammonium, diammonium and triammonium phosphate, monoammonium and diammonium pyrophosphate, monoammonium and diammonium 1-hydroxyethane-1,1-diphosphonic acid as well as monoammonium and diammonium stannate. It is an advantage of this invention that these ammonium salts can be circulated without problems together with the mother liquor and that they do not have to be worked up separately and replenished.

The reaction conditions for performing the ammoximation can be varied within broad limits and can be inferred from the prior art. Hydrogen peroxide can be used in a deficit or excess relative to the carbonyl compound; preferably the molar ratio ranges from 0.5 to 1.5. The molar ratio of hydrogen peroxide to carbonyl compound includes all values and subvalues therebetween, especially including 0.6, 0.7, 0.8, 0.9, 1.0, 1.1, 1.2, 1.3 and 1.4. Ammonia is usually used in an excess relative to hydrogen peroxide as well as in an excess relative to the carbonyl compound. Expediently the molar ratio of ammonia to hydrogen peroxide ranges from 1.5 to 3. The molar ratio of ammonia to hydrogen peroxide includes all values and subvalues therebetween, especially including 1.6, 1.7, 1.8, 1.9, 2, 2.1, 2.2, 2.3, 2.4, 2.5, 2.6, 2.7, 2.8 and 2.9. The ammoximation takes place at a temperature in the range of 25 to 150° C., especially of 50 to 125° C., especially preferably at 60 to 110° C. The temperature of the ammoximation includes all values and subvalues therebetween, especially including 30, 35, 40, 45, 50, 55, 60, 65, 70, 75, 80, 85, 90, 95, 100, 105, 110, 115, 120, 125, 130, 135, 140 and 145° C. Usually the reaction is performed under the pressure established at the chosen temperature, but if necessary the pressure can be raised by the presence of an inert gas, such as nitrogen. Mostly the pressure ranges from 1 to 15 bar (0.1 to 1.5 MPa). The pressure includes all values and subvalues therebetween, especially including 2, 3, 4, 5, 6, 7, 8, 9, 10, 11, 12, 13 and 14 bar.

In the use of a fixed-bed catalyst, the reaction mixture is passed through the reactor or reactors in trickling-bed mode or in bubbling mode, the latter technique being preferred. Preferably the reaction mixture is drawn off from the ammoximation stage and sent to workup when at least 80%, preferably more than 90% of the carbonyl compound has reacted.

By means of the inventive method, and using the particularly preferred n-butanol as solvent, it has become possible in a very simple way to ammoximate even ketones containing 6 or more C atoms, especially 8 to 12 C atoms, in high purity and yield and with high peroxide selectivity, and to discharge water economically out of the process. The method is suitable in particular for continuous operation with few problems. The method is particularly suitable for the continuous synthesis of cyclododecanone oxime.

Having generally described this invention, a further understanding can be obtained by reference to certain specific examples which are provided herein for purposes of illustration only, and are not intended to be limiting unless otherwise specified.

EXAMPLES

Example 1

Ammoximation

A loop reactor with integrated fixed bed and overflow (total volume 530 ml) was packed with 50 g of cylindrical catalyst pellets—formed by extrusion in a diameter of 3 mm and a thickness of 2 mm from titanium silicalite TS-1 together with 20 wt % of aluminum oxide, and produced by the method of European Patent 1138387—and with 50 g of glass balls. Into the reactor there were introduced 350 g of an n-butanolic solution of 87.5 g of cyclododecanone (CDON), 3.2 g of ammonium acetate, 7.0 g of water and 3.5 g of diglyme as internal standard, after which the temperature was stabilized at 80° C. A pressure of 12 bar (1.2 MPa) was established by pressurization with nitrogen. Ammonia was then fed in at 9.5 g/h via a dosing pump; after 15 minutes, hydrogen peroxide (50.0 wt %) was also added at 11.2 g/h via a further proportioning pump.

After 3 hours, continuous operation was begun by starting to feed in a solution of 25 wt % of cyclododecanone in n-butanol at 102.0 g/h.

The overflowing reaction solution was collected in a separator. The CDON conversion was followed during the reaction by gas chromatography, and the hydrogen peroxide concentration was determined by iodometry. Within 20 hours the CDON conversion was about 87.9% and the peroxide selectivity relative to reacted CDON was about 74.7%.

Example 2

Ammoximation

The experiment was carried out in the same way as in Example 1.

The fixed-bed reactor was packed with 50 g of catalyst pellets—spherical agglomerated pellets with a diameter of 2.5 to 3.0 mm, produced from titanium silicalite TS-1 together with 20 wt % of aluminum oxide—and with 50 g of glass balls, and the reaction was maintained for 20 hours. The CDON conversion was 87.7% and the peroxide selectivity relative to reacted CDON was 72.8%.

Example 3

Ammoximation

The experiment was carried out in the same way as in Example 1.

The fixed-bed reactor was packed with 50 g of catalyst pellets—spherical agglomerated pellets with a diameter of 1.0 to 1.4 mm (produced from titanium silicalite TS-1 together with 20 wt % of aluminum oxide)—and with 50 g of glass balls. Continuous operation was maintained for 20 hours: The CDON conversion was 93.2% and the peroxide selectivity relative to reacted CDON was 78.4%.

Example 4

Ammoximation

The feed rates were changed compared with Example 3.

There were fed in ammonia at 7.0 g/h, hydrogen peroxide (50.0 wt %) at 8.2 g/h and an n-butanolic solution of 18.2 g of cyclododecanone, 0.33 g of ammonium acetate, 1.45 g of water and 0.73 g of diglyme as internal standard at 73.0 g/h. Within 70 hours of continuous operation, the CDON conversion was 95.3% and the peroxide selectivity relative to reacted CDON was 81.2%.

Example 5

Crystallization 260 g of the reaction mixture from Example 4 was drained from the separator. At the same time, a large part of the ammonia gas escaping during depressurization was condensed via a cold trap and recycled to the process. The reaction mixture, which had a water content of 10.5 wt %, was cooled to 0° C., and the precipitate that settled out after 3 hours was separated on a suction filter. The precipitate was subsequently washed with a little cold n-butanol and then dried. 44.9 g of oxime was isolated. After the mother liquor had been left to stand, a further 4.5 g of oxime crystallized out.

The total yield of oxime was 49.4 g (88.2% of theory) and the purity was >99.85%.

After the mother liquor and washing solution had been united, the aqueous n-butanol solution still contained about 2.7 g of cyclododecanone, 1.0 g of ammonium acetate, traces of ammonia, 5.9 g of oxime and about 10 wt % of water.

Example 6

Separation of Water From the Mother Liquor 280 g of the n-butanolic mother liquor solution obtained in Example 5 was distilled in order to separate 67 g of a two-phase azeotrope. In the process, the water content was reduced from about 10 wt % in the mother liquor to about 1.4 wt % in the bottom mixture. After distillation, the bottom mixture still contained about 2.7 g of cyclododecanone, 1.0 g of ammonium acetate and 5.9 g of oxime in addition to n-butanol. After addition of cyclododecanone, the bottom mixture was recycled to the ammoximation stage—the conversion and peroxide selectivity remained substantially unchanged.

German patent application 102 60 717.6 filed Dec. 23, 2002, and all patents and other references mentioned herein are incorporated herein by reference.

Numerous modifications and variations on the present invention are possible in light of the above teachings. It is therefore to be understood that within the scope of the appended claims, the invention may be practiced otherwise than as specifically described herein.

What is claimed is:

1. A method for synthesis of an oxime by ammoximation of a carbonyl compound, comprising:
   (i) reacting a carbonyl compound containing 6 to 20 C atoms with ammonia and hydrogen peroxide in the presence of
      a) an organic solvent that is a1) at least partly water-soluble, a2) stable under ammoximation conditions, a3) has a boiling point of higher than 100° C. and/or is capable of forming a two-phase azeotrope with water, and
      b) a titanium-containing heterogeneous catalyst, to obtain a reaction mixture containing said oxime,
   (ii) separating the catalyst from the reaction mixture,
   (iii) crystallizing the oxime and separating the crystallized oxime from the reaction mixture, thereby obtaining crystallized oxime and a mother liquor,
   (iv) if the mother liquor is a two-phase system in which one of the phases is an aqueous phase, then water is removed from the mother liquor in the form of an aqueous phase, and
   (v) distilling off water or a water-containing two-phase azeotrope from the mother liquor, while the distillation bottoms and, optionally, a predominantly organic phase of the azeotrope are recycled to stage (i).

2. The method according to claim 1, wherein said solvent is an alcohol containing 2 to 6 C atoms.

3. The method according to claim 1, wherein said solvent is n-butanol.

4. The method according to claim 1, wherein the crystallizing of the oxime proceeds at a temperature ranging from −40 to +60° C.

5. The method according to claim 1, wherein a linear or cyclic ketone containing 6 to 12 C atoms is ammoximated in the presence of n-butanol as solvent.

6. The method according to claim 1, wherein the ammoximation is performed in the presence of a catalyst containing titanium silicalite.

7. The method according to claim 1, wherein the ammoximation is performed in the presence of a solid acid cocatalyst, a soluble ammonium salt or a combination of a solid acid cocatalyst and a soluble ammonium salt.

8. The method according to claim 1, wherein the ammoximation is performed continuously in one or more fixed-bed reactors connected in series and operated in trickling-bed or bubbling mode at 25 to 150° C.

9. The method according to claim 2, wherein said alcohol containing 2 to 6 C atoms is a monohydric alcohol containing 4 to 6 C atoms or a dihydric alcohol.

10. The method according to claim 1, wherein the crystallizing of the oxime proceeds at a temperature ranging from −10 to +30° C.

11. The method according to claim 1, wherein a linear or cyclic ketone containing 8 to 12 C atoms is ammoximated in the presence of n-butanol as solvent.

12. The method according to claim 1, wherein the ammoximation is performed in the presence of a solid acid cocatalyst selected from the group consisting of $Al_2O_3$, $TiO_2$, $ZrO_2$ and acid zeolites.

13. The method according to claims 1, wherein the ammoximation is performed in the presence of a soluble ammonium salt selected from the group consisting of ammonium nitrate, hydroxylammonium nitrate, ammonium phosphates, ammonium pyrophosphates, ammonium salts of carboxylic acids and ammonium stannates.

14. The method according to claim 1, wherein the ammoximation is performed additionally in the presence of a combination of a) a solid acid cocatalyst selected from the group consisting of $Al_2O_3$, $TiO_2$, $ZrO_2$ and acid zeolites, and b) a soluble ammonium salt selected from the group consisting of ammonium nitrate, hydroxylammonium nitrate, ammonium phosphates, ammonium pyrophosphates, ammonium salts of carboxylic acids and ammonium stannates.

15. The method according to claim 1, wherein the ammoximation is performed continuously in one or more fixed-bed reactors connected in series and operated in trickling-bed or bubbling mode at 50 to 125° C.

16. The method according to claim 1, wherein the distillation bottoms have a water content of from 0.01 to 5 wt %.

17. The method according to claim 1, wherein said titanium-containing heterogeneous catalyst is in the form of pellets.

18. The method according to claim 1, wherein a molar ratio of ammonia to hydrogen peroxide is from 1.5 to 3.

19. The method according to claim 1, wherein a molar ratio of hydrogen peroxide to carbonyl compound is from 0.5 to 1.5.

20. The method according to claim 1, wherein said ammoximation proceeds at a pressure of from 1 to 15 bar.

* * * * *